351-226 SR
1/6/87 OR H 000,185

United States Statutory Invention Registration [19]

[11] Reg. Number: H185
McMahon [43] Published: Jan. 6, 1987

[54] RESPIRATOR PERIMETRY DEVICE

[75] Inventor: Richard W. McMahon, Elkton, Md.

[73] Assignee: The United States of America as represented by the Secretary of the Army, Washington, D.C.

[21] Appl. No.: 801,278

[22] Filed: Nov. 25, 1985

[51] Int. Cl.[4] ..... A61B 3/02
[52] U.S. Cl. ..... 351/226; 351/224

*Primary Examiner*—Stephen C. Buczinski
*Assistant Examiner*—Linda J. Wallace
*Attorney, Agent, or Firm*—Anthony T. Lane; Harold H. Card, Jr.; Edward F. Costigan

[57] ABSTRACT

A device for measuring the field of vision for a person wearing a mask includes a mask support to which the mask can be clamped and which is horizontally movable for aligning one of the subject's eyes with a horizontal axis. A scale support carries a scale member that is rotatably mounted around the horizontal axis and which carries a slidable indicator which can be slid to angles from 0° to 90° with respect to the axis. A mirror is attached to the scale support and lies on the axis for aiding and aligning on the subject's eye with the axis. A pointer is connected to a far end of the scale member and is used to locate the vertical perpendicular position of the subject's eye on the horizontal axis. The scale member is rotatably mounted on the scale support about the horizontal axis and the scale support is movable vertically to bring the horizontal axis into alignment with the subject's eye. The scale support can also be moved horizontally in the direction perpendicular to the horizontal movement of the mask support so that the pointer can be brought into its correct position above the subject's eye. With the device correctly oriented with respect to the subject's eye, the scale member can be brought into a plurality of different rotational positions around the horizontal axis and in each position the indicator used to measuring the maximum field of view from 0° to 90° for the subject's eye.

7 Claims, 3 Drawing Figures

A statutory invention registration is not a patent. It has the defensive attributes of a patent but does not have the enforceable attributes of a patent. No article or advertisement or the like may use the term patent, or any term suggestive of a patent, when referring to a statutory invention registration. For more specific information on the rights associated with a statutory invention registration see 35 U.S.C. 157.

PRIOR ART

RESPIRATOR PERIMETRY DEVICE

STATEMENT OF GOVERNMENT INTEREST

The invention described herein may be manufactured, used and licensed by or for the Government for Governmental purposes without the payment to me of any royalties thereon.

FIELD AND BACKGROUND OF THE INVENTION

The present invention relates in general to testing equipment for testing respirators or gas masks, and in particular to a new and useful perimetry device for measuring the field of view available to a person wearing the respirator or gas mask.

Devices for measuring an individual field of view, perimetry devices, are commercially available. One such device is shown in FIG. 1. This device, however, is meant strictly for testing field of view for a "bare faced" condition. Utilizing such device for an individual wearing a gas mask produces data of questionable accuracy and usefulness. It is very difficult to locate a subject's eye perpendicular with a 90° point on a scale used in the apparatus of FIG. 1, when the subject is wearing a mask. Since the location of the subject's eye is crucial to obtaining a correct field of view reading, the locating process has very low accuracy for the conventional perimetry device. Even if eye location is attained it is virtually impossible to maintain the location for the duration of the test. Accordingly, the test is not readily reproducible. Several subjects were tested with the conventional device while they wore gas masks. Use of the conventional device was abandoned and the invention disclosed here was developed to provide more accurate and reproducible field of view testing.

SUMMARY OF THE INVENTION

The present invention is drawn to a perimetry device which is particularly adapted for use in testing the field of view for an individual wearing a mask, in particular a gas or respirator mask. Accordingly an object of the invention is to provide a device which permits accurate and reproducible field of vision testing for an individual wearing such a mask. Accuracy is estimated to be within ±5°. The inventive device utilizes adJustment on all alignment and location points to obtain maximum accuracy of the data collected.

Accordingly, another object of the present invention is to provide a perimetry device for use in measuring the field of view available when wearing a mask comprising a base, mask mounting means for mounting a mask at a fixed location on the base in a horizontal and a vertical direction, an angle measuring scale having opposite end portions, one end portion mounted for rotation about a horizontal axis which extends through the eye of a person wearing the mask, means connected to the one end of the angle measuring scale for rotating that one end around the axis and for moving that one end vertically with respect to the base, an alignment mirror connected at the axis of rotation for the angle measuring scale for aligning a person's eye with the one end of the scale, a pointer connected to an opposite end of the scale for pointing in a direction perpendicularly to the axis and at the eye of the person wearing the mask, and a vision angle indicator connected to the angle measuring scale for indicating the rotational position of the angle measuring scale around the axis whereby the person's field of view can be measured along the angle measuring scale and at various rotational positions around the axis.

A further object of the invention is to provide such a device wherein the means for holding the mask are horizontally movable in a direction perpendicular to the axis and wherein the means for carrying the angle measuring scale are horizontally movable in a direction parallel to the axis and on the base.

A still further object of the invention is to provide a method of measuring the field of view for a person wearing a mask comprising fixing the mask with respect to an angle measuring device at a fixed vertical and horizontal position with respect to the angle measuring device and measuring the field of view utilizing the angle measuring device with the mask at its fixed position and with the person wearing the mask.

The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which a preferred embodiment of the invention is illustrated.

DESCRIPTION OF THE PREFERRED EMBODIMENT

Figure 1:
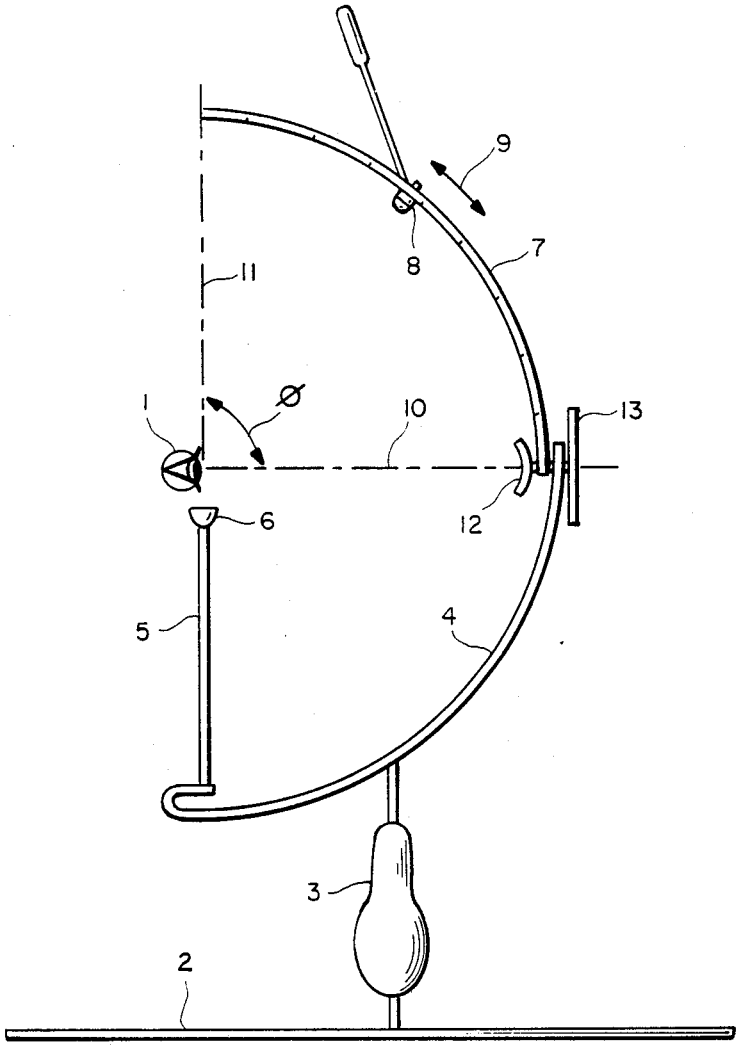
FIG. 1 is a side elevational view of a conventional perimetry device for measuring the field of view of an individual.

Referring first to FIG. 1, a conventional perimetry device is shown for measuring the field of view for a person. Only the person's eye is shown at 1. The device includes a base 2 having a pedestal 3 on which is mounted a curved support 4. A sub-orbital alignment post 5 terminates at an indicator 6 which is positioned immediately under the person's eye. In order to accurately align the person's eye 1 with the positioner 6 he must not be wearing a mask or other obstruction. Otherwise an accurate positioning cannot take place.

An angle measuring scale 7 carries a slidable indicator or uses a separate pointer-like indicator 8 which can slide in a direction of double arrow 9 to any position on scale 7. Scale 7 includes scale markings which are calibrated from zero (at axis 10) to 90° (at axis 11).

An alignment mirror 12 is mounted on support 4 and is positioned at a location to intersect axis 10. In this way the subject can line his eye 1 with the mirror 12. Scale 7 is also fixed to a vision angle indicator 13 and is rotatable about axis 10 on the end of support 1. In operation the subject is positioned with his eye 1 at the intersection of axes 10 and 11. Indicator 8 is moved up scale 7. In the direction of angle $\theta$ ($\theta=90°$) until the person can no longer see the indicator. The measurement is taken down at a zero location on a grid. Scale 7 is then rotated by 30°, for example, or any increment desired, and this new position as read from vision angle indicator 13 is noted on the grid. Indicator 8 is then again slid from its zero position upwardly until the subject can no longer see the indicator. This angle is noted on the grid and again the scale 7 is rotated to a new position. As grid 7 completes its rotation (generally 330°) around axis 10 the subject's field of vision is tabulated.

This conventional equipment cannot however, be used for accurate or for reproducible data when the subject is wearing a gas mask.

Figure 2:
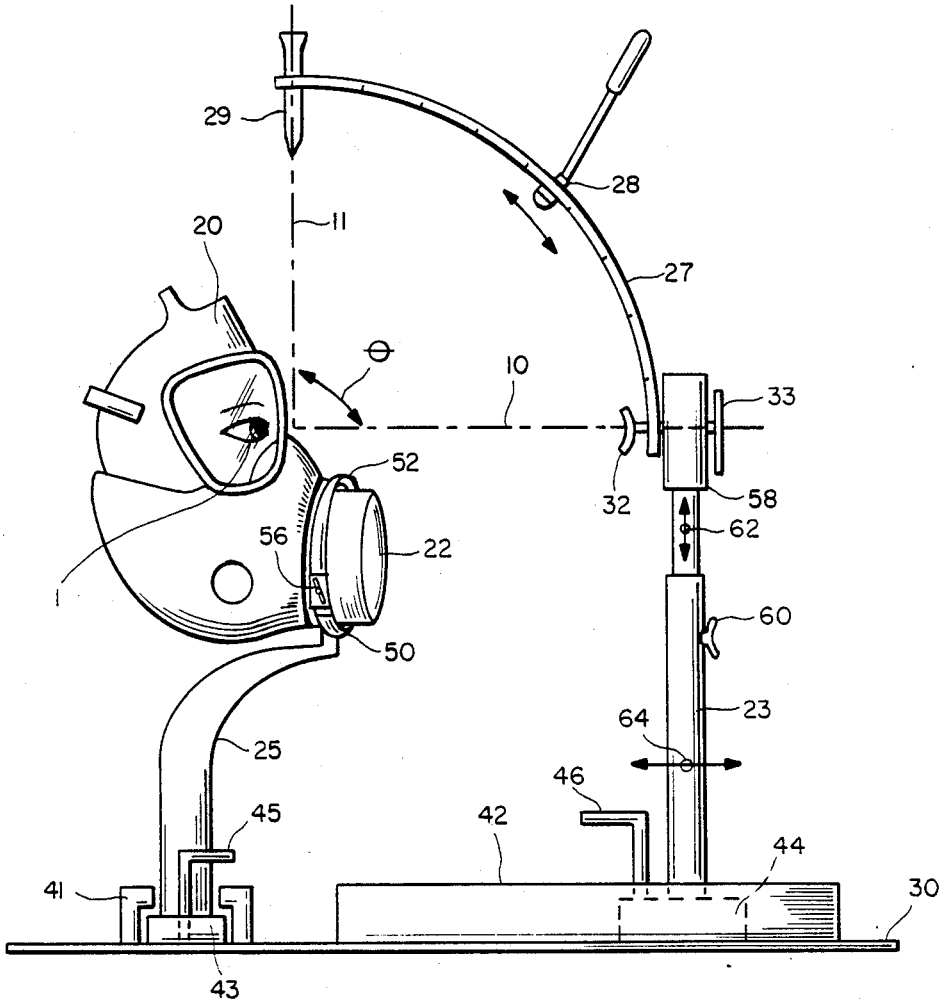
FIG. 2 is a side elevational view of the inventive perimetry device.

FIG. 2 shows the inventive apparatus with an individual, whose eye is again indicated at 1, but this time is wearing a mask 20 having a vision window and a voicemitter 22 through which the individual can speak. An example of this mask is the model M17A1 which comes in various sizes. The invention can be utilized to determine the size which provides the individual with the broadest field of vision.

Figure 3:
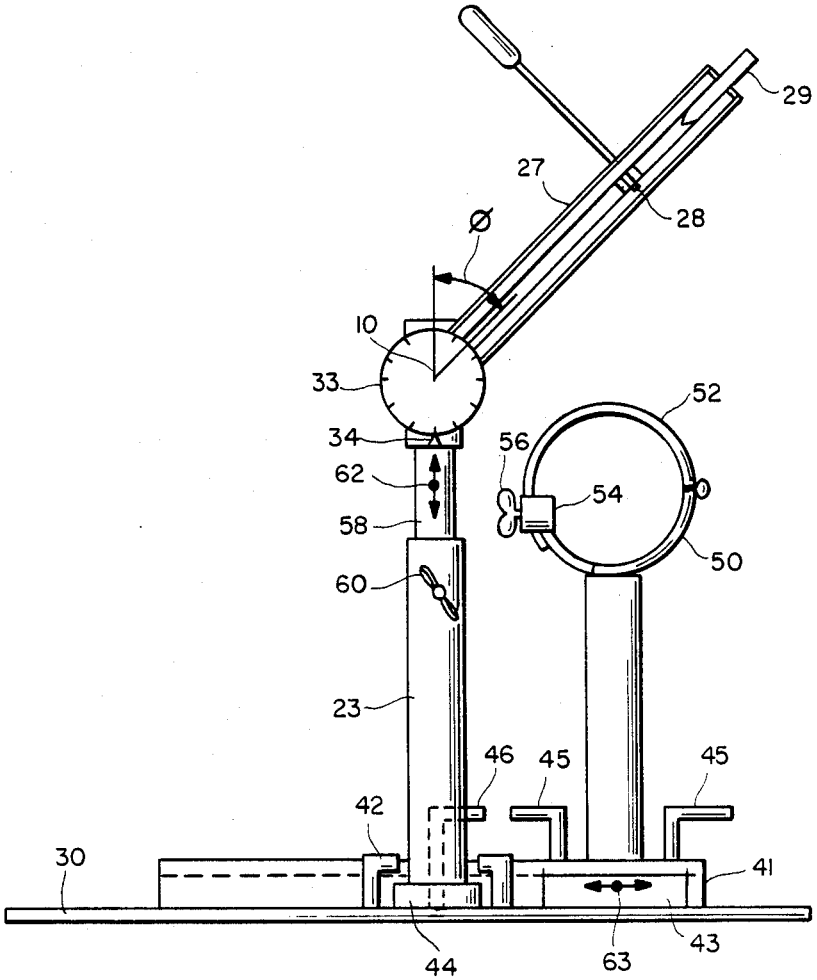
FIG. 3 is a front elevational view of the device shown in FIG. 2 with the mask removed.

The device of the invention as shown in FIGS. 2 and 3 comprises a base 30 which carries two horizontal guideways 41 and 42. A mask support slide 43 is slidably engaged for horizontal movement in the guideway 41 and a scale support slide 44 is slidably mounted for horizontal movement to the guideway 42. Slide 43 can be locked in a selected horizontal position by rotating two lock screws 45 and slide 44 can be locked in a similar manner by rotating a lock screw 46. FIGS. 2 and 3 show how slides 43 and 44 are mounted for horizontal movement in a direction perpendicular to each other.

A mask support 25 is fixed to and extends upwardly from the slide 43 and a post 23 is connected to and extends upwardly from the slide 44.

Mask support 25 includes means for clamping the mask 20 in a fixed position with respect to the device. This includes a lower curved strap 50 to which is hinged an upper curved strap 52. Strap 50 carries a rectangular sleeve 52 in which a free end of strap 52 is insertable. This end of strap 52 can be clamped by a wing nut 56. As shown in FIG. 2, the voicemitter 22 of mask 20 can be clamped between straps 50 and 52 and held there by tightening wing nut 56.

Post 23 carries a vertically slidably mounted scale support 58 whose vertical position can be set by tightening a wing nut 60. Arrow 62 shows the vertical movement which is possible for scale support 58.

An angle measuring scale member 27 which carries scale calibrations from 0° to 90° is rotably mounted to scale support 58. An indicator 28 is slidable to any position within the angular range $\theta$ of 0° to 90°.

A pointer 29 is connected to the far end of scale member 27 and is oriented to point along an axis 11. Axis 11 is perpendicular to the axis 10 which forms the axis of rotation for scale member 27.

Centered on the axis of rotation 10 is a mirror for aligning the subject's eye 1 with the axis 10. A vision angle indicator 33 is mounted for rotation with the scale member 27 and carries a circular scale calibrated from 0° to 330°. This scale can be read with the aid of a mark 34 carried on the scale support 58. FIG. 3 shows the scale member 27 rotated to an angle of 45° with respect to the vertical in a direction of an angle $\theta$. This angle is defined around the horizontal axis 10.

The perimetry device of the invention operates in the following manner. The base 30 is first placed on a horizontal bench or table which is approximately 36 inches high for the comfort of the subject whose field of vision is to be tested. The voicemitter 22 of the mask 20 is then connected to the device by clamping it between straps 50 and 52 and tightening wing nut 56. Before this clamping operation, the subject donns the mask. Lock screws 45 for the mask support 25 are then loosened and slide 43 is brought to a correct horizontal location for bringing either the left or right eye of the subject into approximate alignment with the horizontal axis 10. This movement is in the direction of arrow 63 in FIG. 3. Lock screws 45 are then tightened. Wint nut 60 of post 23 is then loosened and scale support 58 is brought to its correct vertical location to align the subject's eye 1 (with the aid of mirror 32) with the horizontal axis 10. Wing nut 60 is then tightened to fix this vertical position.

Lock screw 46 for post 23 is then loosened and slide 44 is moved horizontally in the direction of arrow 64 along guideway 42. This movement continues until pointer 29 points directly over the subject's eye 1 along vertical axis 11. Lock screw 46 is then tightened and the actual field of vision test can commence. With indicator 33 at its zero angle position with scale member 27 extending vertically above scale support 58, indicator 28 is slid upwardly along scale 27 until the subject can no longer see the indicator. This value is noted in a manner similar to the conventional perimetry device. Indicator 33 is then rotated by 30° for example and again indicator 28, having been returned to its zero angle position, is slide along the scale of scale member 27 until the subject can no longer see it. This test is repeated at desired increments until almost the entire 360° around axis 10 has been covered.

It has been found that the data is highly reproducible and accurate for the field of vision tests.

While a specific embodiment of the invention has been shown and described in detail to illustrate the application of the principles of the invention, it will be understood that the invention may be embodied otherwise without departing from such principles.

What is claimed is:

1. A perimetry device for measuring the field of vision for a subject wearing a mask, comprising:

a base;

a mask support for supporting a mask and which is horizontally movable in a first direction on the base;

a scale support for supporting a scale member, said scale support being mounted for movement to the base in a second horizontal direction;

mask clamping means connected to said mask support for clamping a mask to said mask support;

an angle measuring scale member rotatably mounted to said scale support about a horizontal axis which is parallel to said second horizontal direction, said scale member having an end remote from said scale support;

a pointer connected to said end of said scale member for pointing along an axis which is perpendicular to said horizontal axis and adapted for pointing downwardly at an eye of a subject wearing a mask clamped in said mask clamping means;

a vision indicator slidable along said scale member and viewable by a subject for determining a maximum angular field of vision away from said horizontal axis;

an eye alignment mirror connected to said scale support and lying on said horizontal axis for aiding an alignment of the subject's eye with the horizontal axis; and a vision angle indicator connected to said scale member mounted for rotation with said scale member on said scale support for indicating a rotational position of said scale member around said horizontal axis.

2. A device according to claim 1, including a first guideway connected to said base, a mask support slide slidably mounted in said first guideway in said first horizontal direction, said mask support being connected to said first slide.

3. A device according to claim 2, including a second guideway connected to said base, a scale support slide slidably mounted to said second guideway for movement in said second horizontal direction, said scale support being connected to said scale support slide.

4. A device according to claim 1, including a scale member guideway connected to said base and extending in said second horizontal direction, a scale support slide slidably mounted in said guideway for movement in said second horizontal direction, a post connected to said scale support slide and extending upwardly from said guideway, said scale support being mounted for horizontal movement to said post.

5. A device according to claim 1, including a mask support guideway connected to said base and extending in said first horizontal direction, a mask support slide slidably mounted in said guideway for movement in said second horizontal direction, said mask support being connected to and extending upwardly from said mask support slide, said mask clamping means comprising a lower strap connected to said mask support, an upper strap movably mounted to said lower strap, said upper and lower strap defining an opening for receiving a portion of the mask, and a clamp connected between said upper and lower strap for fixing said upper and lower strap together to move a portion of the mask therebetween.

6. A device according to claim 5, including a scale member guideway connected to said base and extending in said second horizontal direction, a scale support slide slidably mounted in said guideway for movement in said second horizontal direction, a post connected to said scale support slide and extending upwardly from said guideway, said scale support being mounted for horizontal movement to said post.

7. A method of measuring the field of vision for the eye of a subject wearing a mask comprising clamping the mask to a mask support, moving the mask support in a first horizontal direction to align the subject's eye with a selected horizontal axis, supporting an angle measuring scale member on a scale support and for rotation about a rotation axis to the scale support, moving the scale support vertically to align the rotation axis of the scale member with the horizontal axis which is for alignment with the subject's eye, the scale member having an end remote from the scale support with a pointer extending and pointing in a perpendicular axis which is perpendicular to the horizontal axis, moving the scale support in a second horizontal direction which is perpendicular to the first horizontal direction to bring the perpendicular axis into alignment with the subject's eye, and moving the indicator along the scale member from a location near the horizontal axis toward the pointer until the subject can no longer see the indicator.

* * * * *